US006978915B1

(12) United States Patent
Russell

(10) Patent No.: US 6,978,915 B1
(45) Date of Patent: Dec. 27, 2005

(54) AEROSOL VALVE

(75) Inventor: David Joseph Russell, Ware (GB)

(73) Assignee: SmithKline Beecham Corporation, Philadelphia, PA (US)

( * ) Notice: Subject to any disclaimer, the term of this patent is extended or adjusted under 35 U.S.C. 154(b) by 530 days.

(21) Appl. No.: 10/049,014

(22) PCT Filed: Jul. 5, 2000

(86) PCT No.: PCT/EP00/06302

§ 371 (c)(1), (2), (4) Date: Feb. 6, 2002

(87) PCT Pub. No.: WO01/10743

PCT Pub. Date: Feb. 15, 2001

(30) Foreign Application Priority Data

Aug. 7, 1999 (GB) ........................................ 9918573

(51) Int. Cl.[7] ........................................ B65D 83/14
(52) U.S. Cl. ........................................ 222/402.2; 222/402.1
(58) Field of Search ........................................ 222/182, 394, 222/402.1, 402.2, 402.24; 128/200.23

(56) References Cited

U.S. PATENT DOCUMENTS 3,580,431 A 5/1971 Kuffer
5,184,761 A * 2/1993 Lee ........................ 222/402.2
6,095,182 A * 8/2000 Warby ........................ 137/375

FOREIGN PATENT DOCUMENTS

| | | | | |
|---|---|---|---|---|
| DE | 198 35 273 A | | 3/1999 | |
| EP | 0 115 186 A1 | | 8/1984 | |
| EP | 0 317 865 A2 | | 5/1989 | |
| GB | 232351 | | 4/1925 | |
| GB | 2 198 117 A | | 6/1988 | |
| WO | 96 32099 A | | 10/1996 | |
| WO | WO 98/29321 | * | 7/1998 | ........... B65D/83/54 |
| WO | 99 19235 A | | 4/1999 | |
| WO | 99 47195 A | | 9/1999 | |

* cited by examiner

*Primary Examiner*—Gene Mancene
*Assistant Examiner*—Patrick Buechner
(74) *Attorney, Agent, or Firm*—J. Michael Strickland

(57) ABSTRACT

Valve for an aerosol container for a chemical formulation. The valve including a valve body having an inlet port through which the chemical formulation may enter the valve body, an outlet port through which the chemical formulation may exit the valve body, and an open/close mechanism. The open/close mechanism controls flow through the outlet port. The internal surfaces of the valve that come into contact with the chemical formulation include a material with an electrical conductivity greater than $3.8\times10^{7}\Omega^{-1}m^{-1}$.

19 Claims, 3 Drawing Sheets

1
1a
6
16
5
5a
18
2
13
12
19
21
15
3
4
7
7a
4a
9
14
11
17
8
8a
10

AEROSOL VALVE

This application is filed pursuant to 35 U.S.C. §371 as a United States National Phase Application of International Application No. PCT/EP00/06302 filed Jul. 5, 2000, which claims priority from GB 9918573.8 filed Aug. 7, 1999.

TECHNICAL FIELD

This invention relates to a valve and housing for a chemical dispenser, in particular to the properties of the materials comprising the valve and housing assembly.

BACKGROUND TO INVENTION

Chemical dispensers find widespread domestic and industrial application as a convenient means of applying a finite dose of a particular chemical or chemical formulation to a specific target. Typical examples include domestic aerosol containers, industrial paint sprayers, medicament dispensers and agrochemical sprayers.

Medicament dispensers are widely used in the administration of medicines, particularly those for the treatment of respiratory disorders. In dispensing medicaments it is highly desirable that the dose dispensed on each occasion should be consistently at a predetermined level, to ensure that the patient receives the correct dosage. Every effort is therefore made in the design and manufacture of medicament dispensers and their component parts, particularly valve assemblies, to minimise any variations in medicament dosage. However, while great progress has been made in this area in recent years, there is still a risk that on some occasions the requisite dose may not be dispensed. A variety of factors are pertinent in this regard, ranging from lack of uniform dispersal of the formulation to inexperience of the patient in using the device.

One such factor that may occur on occasions, which is of particular relevance to the present invention, is the adherence of medicaments and/or formulation additives to the internal surfaces of the valve and its component parts. This phenomenon is reversible in nature and may lead to greater or lower doses of medicament being dispensed throughout the lifetime of the device. This in turn can result in problems of inconsistent dose administration to the patient and in determining how many effective doses remain within the dispenser. An associated, if minor, problem is that the patient experiences difficulties in manually operating the valve as he perceives a 'notchiness' as the valve stem is depressed and released.

Electrostatic interaction between the chemicals comprising the medicament and/or formulation additives and the internal surface of the valve may be a contributing factor which leads to the problem of dose variation described above. As can be seen from the prior art discussed below, the internal surfaces of these valves are often composed of a variety of materials which may favour electrostatic attraction between the medicament and/or formulation additives and the internal surfaces of the valve. Until now, however, the contributory role electrostatic attraction may have in the adhesion of chemicals to the internal surfaces of the valve has not been recognised and no one has addressed the resulting problem of dose variation in the manner described below.

The prior art teaches that a variety of materials may be used in the manufacture of aerosol valve assemblies. Thus U.S. Pat. No. 3,580,431 describes a method of making aerosol valve tip and stem assemblies from hard materials such as polycarbonates, epoxy resins and metals. UK patent application GB 232351 discloses the use of acetal, nylon, polyester or metal in the preparation of annular lips and flanges in metering valves for pressurised dispensing containers. Similarly UK patent application GB 2198117 describes the construction of the valve body, cup and stem of an aerosol metering device using metal components, while European patent application EP 115186 discloses elements of such valves comprised of metals. Furthermore, valve assemblies consisting of stainless steel stems and aluminium ferrules are known in the prior art (e.g. the 'Spraymiser valve' from 3M Neotechnic Ltd.).

The present invention teaches that construction of the internal surfaces of the valve and those of the supporting housing, either totally or substantially of a highly conductive material, can improve the problems of chemical dose variation and notchiness discussed above. The use of conductive materials in the construction of these surfaces may significantly reduce the build up of electrostatic charge by facilitating electrical discharge to an earthed point and thus ameliorate the aforementioned problems.

SUMMARY OF INVENTION

According to one aspect of the present invention there is provided a valve for an aerosol container for a chemical formulation, the valve comprising a valve body having an inlet port through which the chemical formulation may enter the valve body, an outlet port through which the chemical formulation may exit the valve body and an open/close mechanism by means of which flow through the outlet port is controllable, wherein the internal surfaces of the valve which come into contact with the chemical formulation comprise a material with an electrical conductivity greater than $3.8\times10^{7}\Omega^{-1}m^{-1}$.

In one aspect, the internal surfaces of the valve consist of a material with an electrical conductivity greater than $3.8\times10^{7}\Omega^{-1}m^{-1}$.

In another aspect, the internal surfaces of the valve comprise a coating comprising a material with an electrical conductivity greater than $3.8\times10^{7}\Omega^{-1}m^{-1}$.

In a further aspect, the internal surfaces of the valve comprise a lining comprising a material with an electrical conductivity greater than $3.8\times10^{7}\Omega^{-1}m^{-1}$. Optionally the lining is detachable.

Preferably the internal surfaces of the valve comprise a material with an electrical conductivity greater than $4.0\times10^{7}\Omega^{-1}m^{-1}$. More preferably the internal surfaces comprise a material with an electrical conductivity greater than $4.2\times10^{7}\Omega^{-1}m^{-1}$.

In one aspect, the material comprises a metal or metal alloy. Preferably the metal or metal alloy is selected from the group consisting of copper, stainless steel and brass.

In another aspect, the material comprises a ceramic material. Preferably the ceramic material comprises a cermet material. More preferably the cermet material comprises a composite of a ceramic material with a conductive metal, or a ceramic material doped with a conductive metal. More preferably the cermet material is selected from the group consisting of nickel zirconate, cobalt zirconate and molybdenum zirconate.

In a further aspect, the material comprises an organic polymeric material. Preferably the organic polymeric material is selected from a group consisting of polycarbonate, polyester, acetal, nylon and epoxy resins.

More preferably the organic polymeric material includes a doping element selected from the group consisting of gold, silver and similar precious metals, carbon black and quaternary ammonium salts. The doping elements are taken to include elements which are sputtered, loaded or doped onto a target. Targets can comprise polymeric materials such as polycarbonate, polyester, acetal, nylon or epoxy resins.

In another aspect, the invention provides a slide valve wherein the open/close mechanism comprises a sealing ring and receivable by the sealing ring a valve stem having a dispensing passage, the valve stem being slidably movable within the ring from a valve-closed to a valve-open position in which the interior of the valve body is in communication with the exterior of the valve body via the dispensing passage.

The invention further provides a valve comprising a valve body defining a metering chamber for metering an amount of chemical formulation and an open/close mechanism by means of which the flow through the inlet port to the metering chamber is controllable.

Moreover there is provided a valve wherein the valve body has a sampling chamber in communication with the metering chamber via a second inlet port, the inlet port being controllable by means of an open/close mechanism thereby regulating the flow of chemical formulation into the metering chamber.

In another aspect of the present invention there is provided an aerosol container comprising a valve according to the present invention.

The aerosol container preferably comprises a suspension of a chemical in a propellant. Preferably the propellant in the aerosol container is liquified HFA134a or HFA-227.

Preferably the chemical is a medicament. More preferably the medicament in the aerosol container is selected from the group consisting of albuterol, salmeterol, ipratropium bromide, fluticasone propionate, beclomethesone dipropionate, salts or solvates thereof and any combination thereof. A preferred combination comprises salmeterol xinafoate and fluticasone propionate.

In one aspect, the chemical is an agrochemical. Preferably the agrochemical is selected from the group consisting of herbicide, insecticide, fungicide, rodenticide, nematocide, acaracide and plant growth regulator.

In another aspect, the chemical is a crop fertiliser.

In a further aspect, the chemical is a marking material. Preferably the marking material is selected from the group consisting of ink, dye and pigment.

In another aspect, the chemical is a covering material. Preferably the covering material is selected from the group consisting of paint, dye, pigment, preservative, corrosion inhibitor and static inhibitor.

In a further aspect, the chemical is a deodorant or a perfume.

In yet another aspect, the chemical is a cosmetic.

In a further aspect, the chemical is a hair spray for holding hair in place.

In one aspect, the chemical is an air freshener.

In another aspect, the chemical is a cleanser for cleaning and polishing surfaces.

In a further aspect, the chemical is a lubricant, such as a light oil, for lubricating surfaces.

In one aspect there is provided an aerosol container, wherein the internal surfaces comprise a material with an electrical conductivity greater than $3.8\times10^{7}\Omega^{-1}m^{-1}$. Preferably the internal surfaces comprise a material with an electrical conductivity greater than $4\times10^{7}\Omega^{-1}m^{-1}$. More preferably the internal surfaces comprise a material with an electrical conductivity greater than $4.2\times10^{7}\Omega^{-1}m^{-1}$.

According to another aspect of the present invention there is provided a housing for an aerosol container, the container having an outlet member for dispensing of aerosol therefrom, comprising a sleeve portion for receipt of the container, a support for receipt of the outlet member, the support having a dispensing passage through which the aerosol is dispensable, wherein the surfaces of the housing comprise a material with an electrical conductivity greater than $3.8\times10^{7}\Omega^{-1}m^{-1}$.

In one aspect, the surfaces of the housing consist of a material with an electrical conductivity greater than $3.8\times10^{7}\Omega^{-1}m^{-1}$.

In another aspect, the surfaces of the housing comprise a coating comprising a material with an electrical conductivity greater than $3.8\times10^{7}\Omega^{-1}m^{-1}$.

Preferably the surfaces of the housing comprise a material with an electrical conductivity greater than $4\times10^{7}\Omega^{-1}m^{-1}$. More preferably the surfaces of the housing comprise a material with an electrical conductivity greater than $4.2\times10^{7}\Omega^{-1}m^{-1}$.

Optionally the surfaces of the housing comprise a ceramic material. Preferably the ceramic material comprises a cermet material. More preferably the cermet material comprises a composite of a ceramic material with a conductive metal, or a ceramic material doped with a conductive metal. The cermet material is selected from the group consisting of nickel zirconate, cobalt zirconate and molybdenum zirconate.

In another aspect, the surfaces of the housing comprise an organic polymeric material. Preferably the organic polymeric material is selected from the group consisting of polycarbonate, polyester, acetal, nylon and epoxy resins.

More preferably the organic polymeric material includes a doping element selected from the group consisting of gold, silver and similar precious metals, carbon black and quaternary ammonium salts. The doping elements are taken to include elements which are sputtered, loaded or doped onto a target. Targets can comprise polymeric materials such as polycarbonate, polyester, acetal, nylon or epoxy resins.

According to another aspect of the present invention there is provided a chemical dispenser comprising an aerosol container and a housing as herein described.

According to a further aspect of the present invention, there is provided a chemical dispenser comprising a reservoir for a chemical in aqueous solution or suspension; a pressurised canister for aerosolising the chemical solution or suspension; a chamber wherein the solution or suspension is aerosolisable by release of pressure from the canister, the chamber having a dispensing passage through which aerosol is dispensable; wherein the surfaces of the reservoir and/or the chamber and/or the dispensing passage comprise a material with an electrical conductivity greater than $3.8\times10^{7}\Omega^{-1}m^{-1}$.

BRIEF DESCRIPTION OF DRAWINGS

The invention will now be described with reference to the accompanying drawings in which.

DETAILED DESCRIPTION OF DRAWINGS

Figure 1:
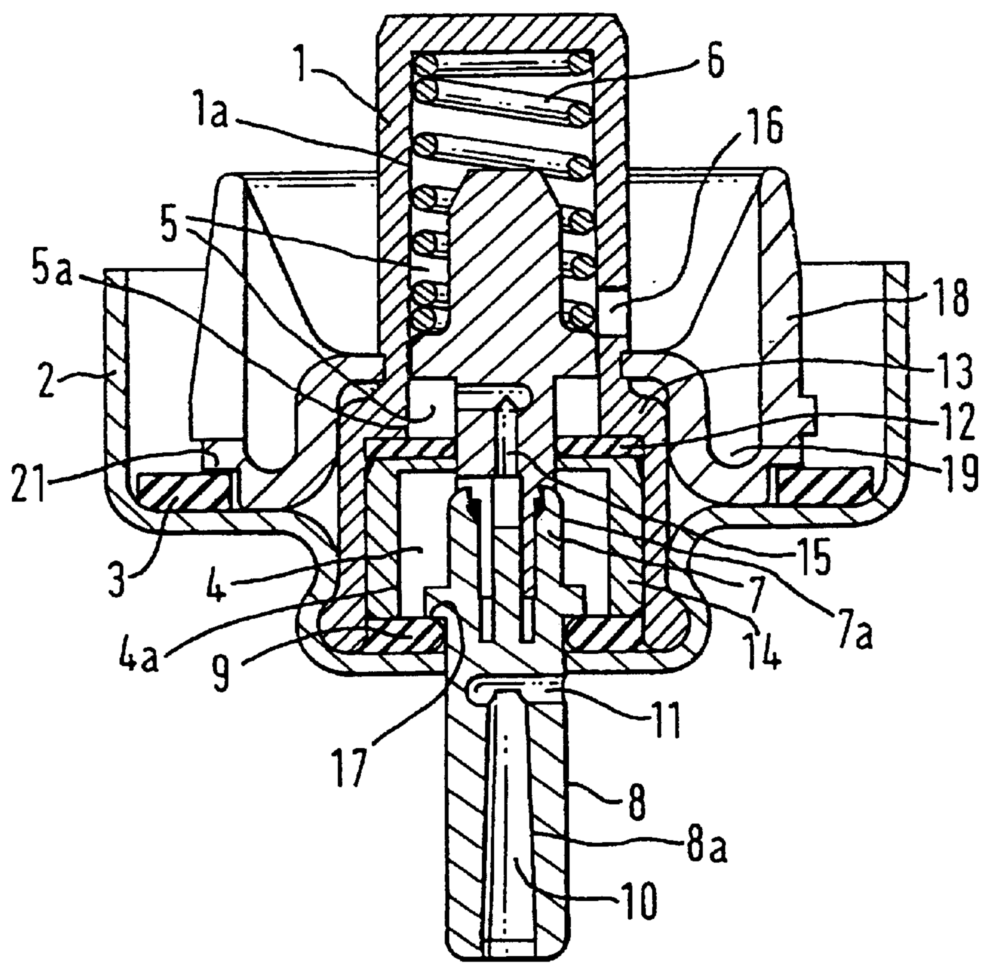
FIG. 1 is a section through a metering valve according to the invention.

A valve according to the invention is shown in FIG. 1 and comprises a valve body 1 sealed in a ferrule 2 by means of crimping, the ferrule itself being set on the neck of a container (not shown) with interposition of a gasket 3 in a well-known manner. The container is loadable with a suspension of medicament, such as salmeterol xinafoate in liquid propellant HFA134a.

The valve body 1 is formed at its lower part with a metering chamber 4, and its upper part with a sampling chamber 5 which also acts as a housing for a return spring 6.

The words "upper" and "lower" are used for the container when it is in a use orientation with the neck of the container and valve at the lower end of the container which corresponds to the orientation of the valve as shown in FIG. 1. Inside the valve body 1 is disposed a valve stem 7, a part 8 of which extends outside the valve through lower stem seal 9 and ferrule 2. The stem part 8 is formed with an inner axial or longitudinal canal 10 opening at the outer end of the stem and in communication with a radial passage 11.

The upper portion of stem 7 has a diameter such that it can pass slidably through an opening in an upper stem seal 12 and will engage the periphery of that opening sufficiently to provide a seal. The stem seals 9 and 12 are made by a moulding process and have rounded points of contact with the valve stem 7. Upper stem seal 12 is held in position against a step 13 formed in the valve body 1 between the said lower and upper parts by a sleeve 14 which defines the metering chamber 4 between lower stem seal 9 and upper stem seal 12. The valve stem 7 has a passage 15 which, when the stem is in the inoperative position shown, provides a communication between the metering chamber 4 and sampling chamber 5, which itself communicates with the interior of the container via orifice 16 formed in the side of the valve body 1.

Valve stem 7 is biased downwardly to the inoperative position by return spring 6 and is provided with a shoulder 17 which abuts against lower stem seal 9. In the inoperative position as shown in FIG. 1 shoulder 17 abuts against lower stem seal 9 and radial passage 11 opens below lower stem seal 9 so that the metering chamber 4 is isolated from canal 10 and suspension inside cannot escape.

A ring 18 having a "U" shaped cross section extending in a radial direction is disposed around the valve body below orifice 16 so as to form a trough 19 around the valve body. As seen in FIG. 1 the ring is formed as a separate component having an inner annular contacting rim of a diameter suitable to provide a friction fit over the upper part of valve body 1, the ring seating against step 13 below the orifice 16. However, the ring 18 may alternatively be formed as an integrally moulded part of valve body 1.

The principal internal surfaces of the valve of FIG. 1 are comprised of stainless steel which has a conductivity greater than $3.8\times10^{7}\Omega^{-1}m^{-1}$. Thus, the internal surfaces of the valve body (1*a*), metering chamber (4*a*), sampling chamber (5*a*) and valve stem (7*a* and 8*a*) are comprised of stainless steel. These surfaces may in other embodiments be comprised of, consist of, be coated with, or be lined with another material having a conductivity greater than $3.8\times10^{7}\Omega^{-1}m^{-1}$. The material can be a metal or metal alloy, a ceramic material or composite, or alternatively an organic polymeric material.

To use the device the container is first shaken to homogenise the suspension within the container. The user then depresses the valve stem 7 against the force of the spring 6. When the valve stem is depressed both ends of the passage 15 come to lie on the side of upper stem seal 12 remote from the metering chamber 4. Thus a dose is metered within the metering chamber. Continued depression of the valve stem will move the radial passage 11 into the metering chamber 4 while the upper stem seal 12 seals against the valve stem body. Thus, the metered dose can exit through the radial passage 11 and the outlet canal 10.

Releasing the valve stem causes it to return to the illustrated position under the force of the spring 6. The passage 15 then once again provides communication between the metering chamber 4 and sampling chamber 5. Accordingly, at this stage liquid passes under pressure from the container through orifice 16, through the passage 15 and thence into the metering chamber 4 to fill it.

Figure 2:
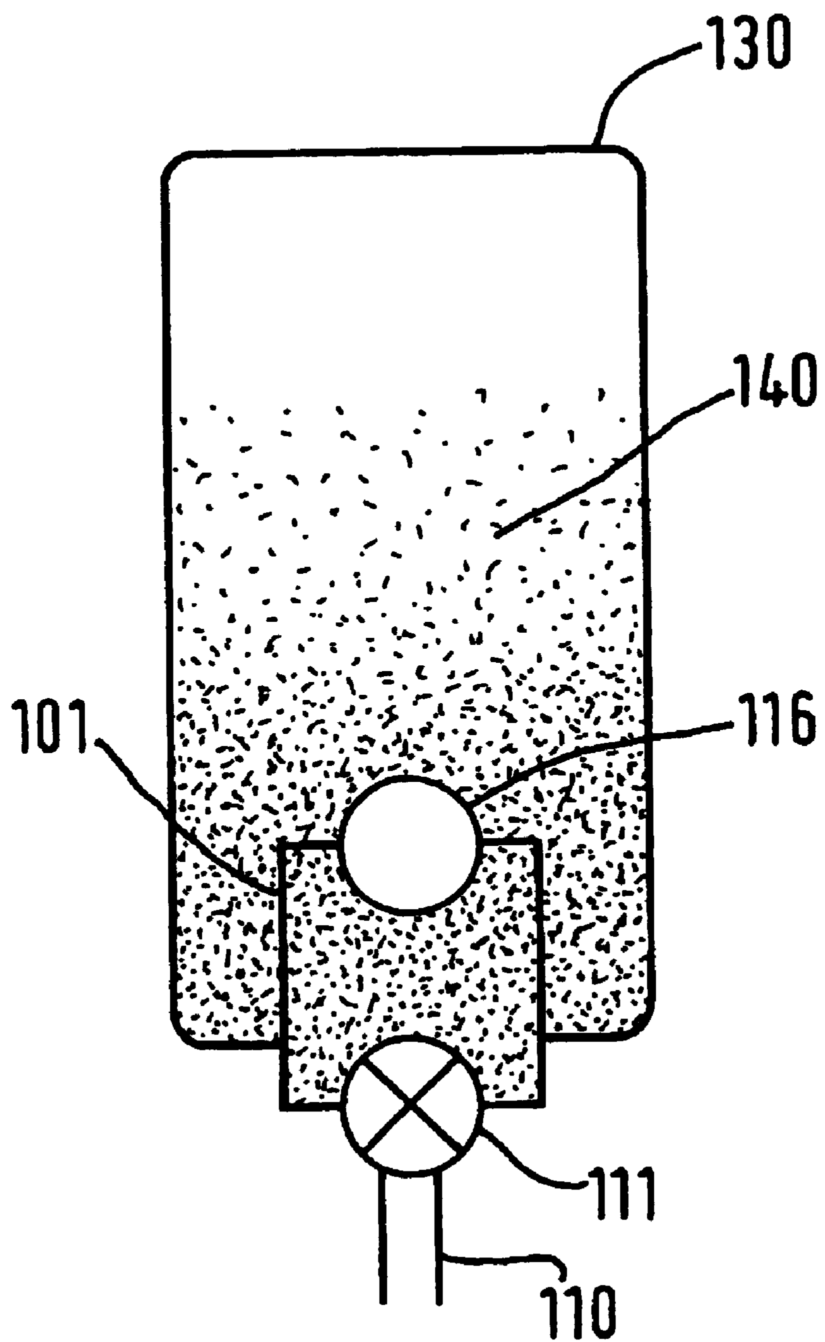
FIG. 2 is a schematic representation of a section through an aerosol container and valve according to the invention.

A schematic diagram of a section through an aerosol container and valve according to the invention is shown in FIG. 2. As illustrated, valve body 101 is attached to aerosol container 130 which is filled with a medicament formulation 140. The container is loadable with a suspension of medicament, such as salmeterol xinafoate in liquid propellant HFA134a.

To use the device the container is first shaken to homogenise the suspension within the container. Medicament formulation 140 enters the valve body 101 from container 130 via the inlet port 116 and is discharged from the valve via the outlet port 111 along outlet canal 110 by means of an open/close mechanism.

Figure 3:
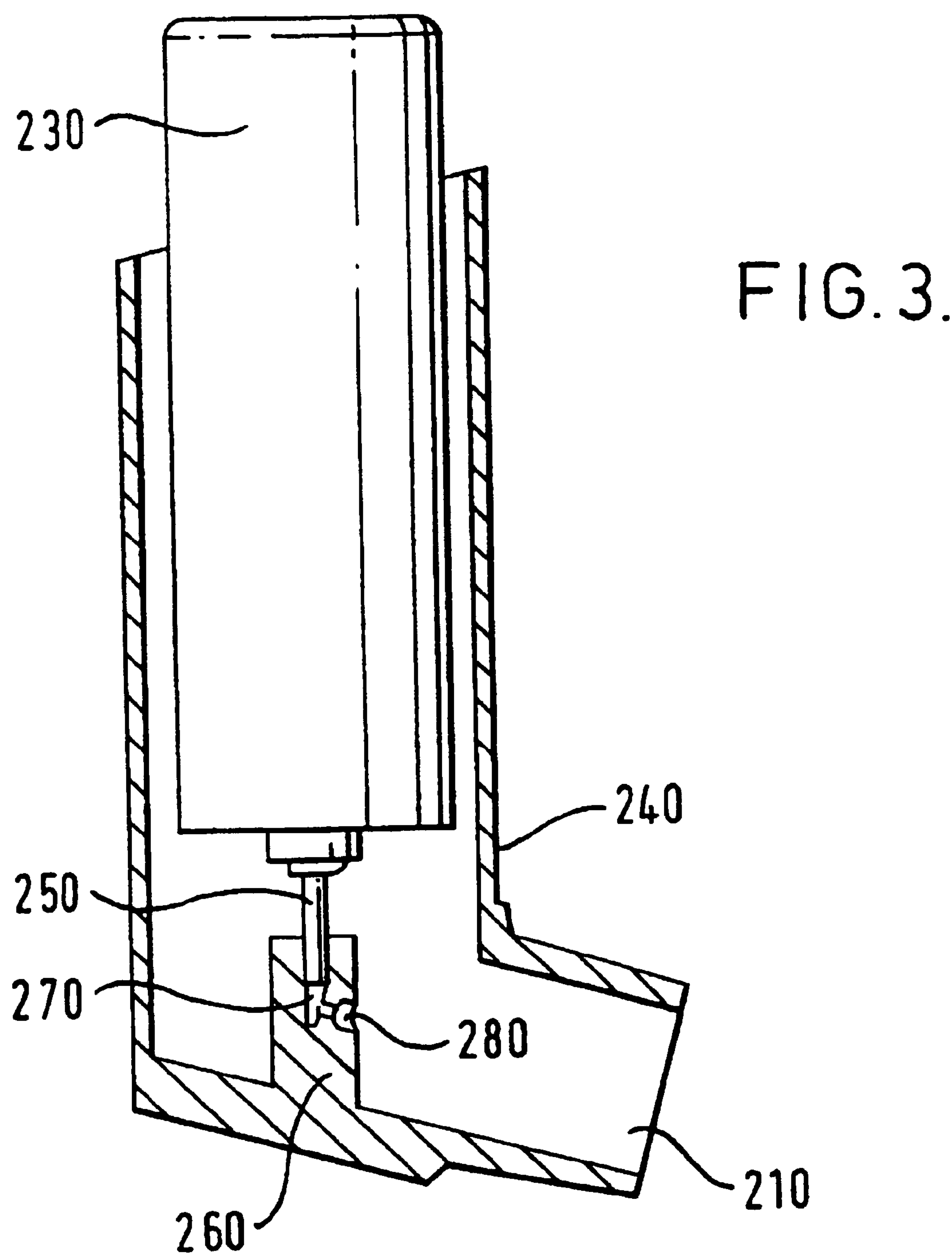
FIG. 3 is a sectional view of a medicament dispenser according to the invention.

A medicament dispenser comprising an aerosol container and housing according to the invention is shown in FIG. 3. The housing may comprise, consist of, or be coated with a material with a conductivity greater than $3.8\times10^{7}\Omega^{-1}m^{-1}$. The medicament dispenser comprises a tubular housing 240, open at both ends, in which an aerosol container 230 can be located (considered to be the top of the device). An outlet 210 leads laterally from the lower end of the housing 240 and can be in the form of a mouthpiece or, if desired, a nozzle for insertion into the patient's nostril. The aerosol container 230 has an outlet valve stem 250 at one end which can be depressed to release a measured dose of medicament. The valve may be the valve of FIG. 1.

A support 260 is provided at the lower end of the housing 240 and has a passage 270 in which the valve stem 250 of the aerosol container 230 can be located and supported. A second passage 280 is provided in the support 260 and is directed towards the interior of the outlet 210.

To use the dispenser the device is shaken to homogenise the suspension within the container. The protruding portion of the aerosol container 230 can then be depressed to move the container relative to the valve stem 250 to open the valve and a dose of medicament contained in the aerosol will be discharged through the passage 280 and into the outlet 210 from which it can be inhaled by the patient. One dose will be released from the aerosol container each time it is fully depressed.

In particular, the dispenser is suitable for containing medicament for the treatment of respiratory disorders. Appropriate medicaments may thus be selected from, for example, analgesics, e.g., codeine, dihydromorphine, ergotamine, fentanyl or morphine; anginal preparations, e.g., diltiazem; antiallergics, e.g., cromoglycate, ketotifen or nedocromil; antiinfectives e.g., cephalosporins, penicillins, streptomycin, sulphonamides, tetracyclines and pentamidine; antihistamines, e.g., methapyrilene; anti-inflammatories, e.g., beclomethasone dipropionate, fluticasone propionate, flunisolide, budesonide, rofleponide, mometasone furoate, ciclesonide or triamcinolone acetonide; antitussives, e.g., noscapine; bronchodilators, e.g., albuterol, salmeterol, ephedrine, adrenaline, fenoterol, formoterol, isoprenaline, metaproterenol, phenylephrine, phenylpropanolamine, pirbuterol, reproterol, rimiterol, terbutaline, isoetharine, tulobuterol or 4-hydroxy-7-[2-[[2-[[3-(2-phenylethoxy)propyl]sulfonyl]ethyl]amino]ethyl-2(3)-benzothiazolone; diuretics, e.g., amiloride; anticholinergics, e.g., ipratropium, tiotropium, atropine or oxitropium; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagon; vaccines, diagnostics, and gene therapies. It will be clear to a person skilled in the art that, where appropriate, the medicaments may be used in the form of salts, (e.g., as alkali metal or amine salts or as acid addition salts) or as esters (e.g., lower alkyl esters) or as solvates (e.g., hydrates) to optimise the activity and/or stability of the medicament and/or to minimise the solubility of the medicament in the propellant.

Preferred medicaments are selected from albuterol, salmeterol, ipratropium bromide, fluticasone propionate and beclometasone dipropionate and salts or solvates thereof, e.g., the sulphate of albuterol and the xinafoate of salmeterol.

Medicaments can also be delivered in combinations. Preferred formulations containing combinations of active ingredients contain salbutamol (e.g., as the free base or the sulphate salt) or salmeterol (e.g., as the xinafoate salt) in combination with an antiinflammatory steroid such as a beclomethasone ester (e.g., the dipropionate) or a fluticasone ester (e.g., the propionate). A particularly preferred combination comprises salmeterol xinafoate salt and fluticasone propionate.

It will be understood that the present disclosure is for the purpose of illustration only and the invention extends to modifications, variations and improvements thereto.

The application of which this description and claims form part may be used as a basis for priority in respect of any subsequent application. The claims of such subsequent application may be directed to any feature or combination of features described therein.

What is claimed is:

1. A drug product comprising:

a canister containing a suspension comprising a medicament suspended in a propellant in communication with a valve body defining a metering chamber and having an inlet port and an outlet port;

a valve stem having an internal canal; and one or more gaskets for sealing the valve stem, wherein the internal surfaces of the valve that contact the suspension include a material free of fluoropolymer having an electrical conductivity greater than $3.8\times10^7\Omega^{-1}m^{-1}$.

2. The drug product according to claim 1, wherein the internal surfaces of the valve include a coating having an electrical conductivity greater than $3.8\times10^7\Omega^{-1}m^{-1}$.

3. The drug product according to claim 1, wherein said valve body includes a detachable lining.

4. The drug product according to claim 1, wherein the material has an electrical conductivity greater than $4\times10^7\Omega^{-1}m^{-1}$.

5. The drug product according to claim 1, wherein the material has an electrical conductivity greater than $4.2\times10^7\Omega^{-1}m^{-1}$.

6. The drug product according to claim 1, wherein the material comprises a metal or metal alloy.

7. The drug product according to claim 1, wherein the material comprises an organic polymer.

8. The drug product according to claim 1, wherein the one or more gaskets includes a sealing ring sealing the valve stem and wherein the valve stem is slidably movable within the sealing ring from a closed to an open position, whereby the interior of the valve body is in communication with the exterior of the valve body via said canal.

9. The drug product of claim 1, wherein the propellant is HFA134a or HFA227.

10. The drug product of claim 1, wherein the medicament is a salt, solvate or ester of fluticasone.

11. The drug product of claim 1, wherein said medicament is selected from the group consisting of albuterol, salmeterol, ipratropium, fluticasone, beclomethasone, a salt, solvate or ester thereof and combinations thereof.

12. The drug product of claim 1, wherein the medicament is a combination of salmeterol xinafoate and fluticasone propionate.

13. The drug product of claim 1, further comprising an actuator including a sleeve for receiving said container and a support for receiving the valve stem, said support having a dispensing passage.

14. The drug product according to claim 1, wherein the valve body defines a metering chamber for metering an amount of suspension.

15. The drug product according to claim 14, wherein said valve body further defines a sampling chamber in communication with the metering chamber.

16. The drug product according to claim 1, wherein the material comprises a ceramic.

17. The drug product according to claim 16, wherein said ceramic includes a cermet.

18. The drug product according to claim 17, wherein said cermet includes a composite of ceramic and a conductive metal or a ceramic doped with a conductive metal.

19. The drug product according to claim 18, wherein the cermet is nickel zirconate, cobalt zirconate or molybdenum zirconate.

* * * * *